United States Patent [19]

Tomita et al.

[11] Patent Number: 5,506,113
[45] Date of Patent: Apr. 9, 1996

[54] MEASURING COMPOSITION

[75] Inventors: Kosuke Tomita; Yasunobu Hashimoto, both of Kyoto, Japan

[73] Assignee: Unitika Ltd., Hyogo, Japan

[21] Appl. No.: 467,891

[22] Filed: Jun. 6, 1995

Related U.S. Application Data

[63] Continuation of Ser. No. 278,253, Jul. 20, 1994, abandoned, which is a continuation of Ser. No. 70,052, Jun. 1, 1993, abandoned, which is a continuation of Ser. No. 747,407, Aug. 19, 1991, abandoned, which is a continuation of Ser. No. 627,911, Dec. 17, 1990, abandoned, which is a continuation of Ser. No. 580,503, Feb. 15, 1984, abandoned.

[30] Foreign Application Priority Data

Feb. 16, 1983 [JP] Japan .................................. 58-25249

[51] Int. Cl.⁶ .................................. C12Q 1/54; C12Q 1/32
[52] U.S. Cl. .................................. 435/14; 435/15; 435/17; 435/26
[58] Field of Search .................................. 435/14, 15, 17, 435/26

[56] References Cited

U.S. PATENT DOCUMENTS 4,271,264  6/1981  Modrovich .................................. 435/14
4,438,199  3/1984  Miwa et al. .................................. 435/190

OTHER PUBLICATIONS

Walker et al (1966) Glucokinase "Methods in Enzgmology" 9:381–8 Academic Press.

Kruse et al, *Tissue Culture Methods and Applications,* Academic Press, New York, 685 (1973).

Walker et al, "Glucokinase", Methods Of Enzymology, vol. 9, pp. 381–388 (1966) Academic Press.

Kamel et al, "An Ultraspecific Micromethod for Determination of Deglycose", Analytical Biochemistry, 18, 270–273 (1967).

*Primary Examiner*—Ralph J. Gitomer
*Attorney, Agent, or Firm*—Sughrue, Mion, Zinn, Macpeak & Seas

[57] ABSTRACT

A measuring composition for use in determination of glucose, ATP, phosphotransferases such as creatine phosphokinase, and glucosidases is disclosed. The composition is comprised of glucokinase, glucose-6-phosphate dehydrogenase, and potassium or ammonium ions. This composition makes it possible to shorten measuring times even if the amount of enzyme is reduced, and exhibits high stability when stored at room temperature in a solution state.

15 Claims, 1 Drawing Sheet

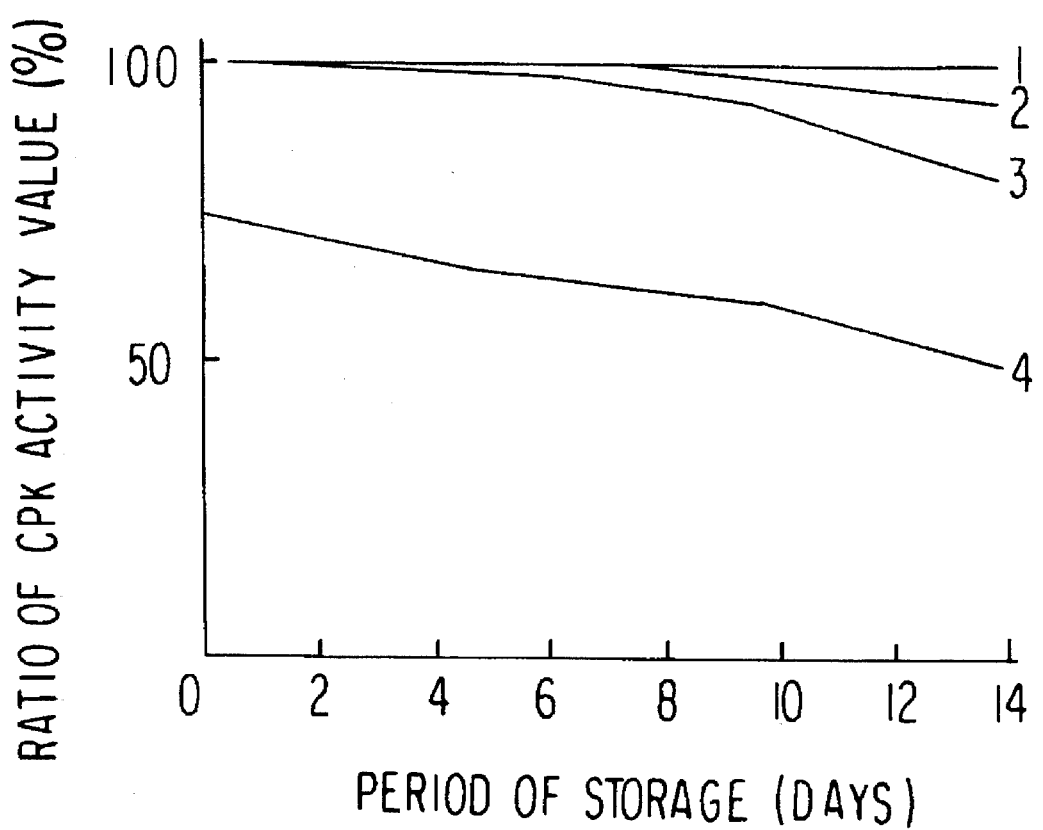

MEASURING COMPOSITION

This is a continuation of application Ser. No. 08/278,253, filed Jul. 20, 1994, now abandoned, which is a continuation application of application Ser. No. 08/070,052, filed Jun. 1, 1993, now abandoned, which is a continuation application of application Ser. No. 07/747,407, filed Aug. 19, 1991, now abandoned, which is a continuation application of application Ser. No. 07/627,911, filed Dec. 17, 1990, now abandoned, which is a continuation application of application Ser. No. 06/580,503, filed Feb. 15, 1984, now abandoned.

FIELD OF THE INVENTION

The present invention relates to a measuring composition and, more particularly, to a composition for use in determination of glucose, adenosine triphosphate (ATP), phosphotransferases such as creatine phosphokinase (CPK), enzymes (GA) which can hydrolyze the substrates consisting of glycosidic bond, etc.

BACKGROUND OF THE INVENTION

In the field of clinical analysis, a method utilizing coupling enzymes of glucokinase (GK) and glucose-6-phosphate dehydrogenase (G6PDH), i.e., a so-called GK/G6PDH coupling enzyme system, has heretofore been employed in determination of glucose or CPK.

This method is based on the following principle:

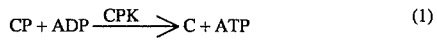  (1)

  (2)

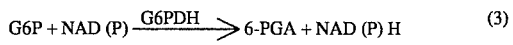  (3)

The symbols used in the above formulae are defined as follows:
CP: creatine phosphate
C: creatine
ADP: adenosine-5'-diphosphate
ATP: adenosine-5'-triphosphate
G6P: glucose-6-phosphate
NAD(P): oxidized form nicotinamide adenine dinucleotide (phosphate)
NAD(P)H: reduced form nicotinamide adenine dinucleotide (phosphate)
6-PGA: 6-phosphogluconate The above-described reactions (1), (2) and (3) are catalyzed by CPK, GK and G6PDH, respectively. Thus, the CPK measurement follows the equations (1), (2) and (3), and the lucose measurement, the equations (2) and (3).

Conventional glucose or CPK-measuring compositions utilizing the HK/G6PDH coupling enzyme system are of low stability when stored at room temperature in the form of solution and their service lives as reagents at room temperature (18°–35° C.) after dissolving are very short, as described in *Methods in Enzymatic Analysis,* 2nd English Edition, ed. by Hans Ulrich Bergmeyer (published by Verlag Chemie International), pages 789–793 and 1196–1205 (1974). Thus, an improved measuring composition using heat stable GK has been developed, as described in Japanese Patent Application (OPI) No. 169598/81 (corresponding to U.S. patent application Ser. No. 267,245, now U.S. Pat. No. 4,438,199, and also to EPC Patent Publication No. 43181) (the term "OPI" as used herein means a "published unexamined Japanese patent application").

The above-proposed composition is improved in storage stability at room temperature compared with conventional compositions. Its stability, however, is not sufficiently satisfactory because of instability of coupling enzyme and SH-containing compound contained in the composition. Furthermore, to keep the stability over long periods of time, it is necessary to add a relatively large amount of enzyme. Use of such a large amount of enzyme does not cause any serious problem. However, as the amount of enzyme to be used is decreased, the problem of a drop in rate of reaction and, in its turn, an increase in the time required for the measurement arises. Although this problem is not noticeable in measuring the individual activity of GK and G6PDH, it becomes seriously noticeable when the composition is used in determination of glucose or CPK. This is one of the causes preventing practical use of the composition.

Addition of potassium chloride (KCZ) in the assay mixture or purification medium of GK is described in *Methods in Enzymology,* published by Academic Press Inc., Vol. 9, pages 381–388 (1966). It is also described that although KCl possesses an action to stabilize GK, while not exerting influences on the rate of reaction (Vm).

SUMMARY OF THE INVENTION

An object of the invention is to provide a measuring composition which makes it possible to shorten the measuring time even if the amount of enzyme being used is reduced and, furthermore, which can be stored at room temperature over long periods of time.

It has been found that the above objects are attained by incorporating potassium or ammonium ions into the composition.

The present invention relates to a measuring composition comprising glucokinase and glucose-6-phosphate dehydrogenase, characterized in that it further contains potassium and/or ammonium ions.

In the measuring composition of the invention, the potassium or ammonium ions activate the coupling enzyme reaction. Thus, the incorporation of the potassium or ammonium ions makes it possible to shorten the measuring time even if the amount of enzyme used in the measuring composition is decreased and, furthermore, to increase the stability at room temperature of the composition while it is in solution.

BRIEF DESCRIPTION OF THE DRAWING

The Figure is a graph illustrating the storage stability of each CPK-measuring composition prepared in Examples 3 and 4, and Comparative Examples 3 and 4. This storage stability is presented by plots of the ratio of CPK activity value of control serum as determined using each CPK-measuring composition after its storage for a given period of time to that as determined using a fresh CPK-measuring composition prepared in Example 3 versus the period of storage. Curves 1, 2, 3 and 4 represent the storage stability of CPK-measuring compositions prepared in Examples 3 and 4, and Comparative Examples 3 and 4, respectively.

DETAILED DESCRIPTION OF THE INVENTION

Various types of GK and G6PDH resulting from microorganisms or animals can be used in the present invention. In particular, GK and G6PDH produced by microorganisms having the optimum growth temperature of 50° to 85° C. are preferred from a viewpoint of stability. These microorganisms include those belonging to the genus Bacillus such as *Bacillus stearothermophilus, Bacillus thermoproteolytic,* and *Bacillus acidocaldarius,* genera Thermoactinomyces, Thermus and Thermomicrobium. Particularly preferred is *Bacillus stearothermophilus.* Suitable examples are ATCC 7953, 7954, 8005, 10149, 12980, and NCA 1503.

G6PDH is not critical in its source as in GK. It is preferably G6PDH produced by, for example, *Leuconostoc mesenteroides* and *Pseudomonas fluorescens,* which acts not only on NADP but also on NAD as a coenzyme. More preferred is heat stable G6PDH produced by thermophilic microorganisms, which acts on both NAD and NADP and is superior in stability and storage properties.

With regard to extraction, purification, etc., in the preparation of GK and G6PDH, the known techniques as described in *Methods in Enzymology,* Vol. 9, pages 381 to 388 and 116–131 (1966), British Patent 2,066,261 and Canadian Patent 1,156,570 can be used appropriately in combination with each other.

It is essential for the measuring composition of the invention to contain potassium or ammonium ions. The concentration of potassium and/or ammonium ions to be incorporated is at least 0.1 mM, preferably at least 0.2 mM and more preferably at least 0.5 mM per based on the solution of the measuring composition. If the potassium and/or ammonium ion concentration is less than 0.1 mM, the effects of the present invention cannot be obtained. On the other hand, if it is in excess of 2M, no further increase in the effects is obtained and it is rather uneconomical.

Incorporation of potassium or ammonium ions into the composition can be attained by using compounds producing potassium or ammonium ions when dissolved in water. Any compounds can be used for this purpose as long as they can produce potassium or ammonium ions when dissolved in water. Examples are salts of inorganic acids, such as carbonic acid, hydrochloric acid, sulfuric acid, nitric acid, phosphoric acid, and boric acid, and salts of monocarboxylic acids, such as acetic acid and propionic acid, dicarboxylic acids, such as malonic acid and succinic acid, amino acids, such as glycine and alanine, oxyacids, such as glycolic acid and lactic acid, and organophosphoric acids, such as glycerophosphoric acid. Of these compounds, the salts of carbonic acid, hydrochloric acid, sulfuric acid, phosphoric acid, and acetic acid are preferred. Particularly preferred are the salts of hydrochloric acid and sulfuric acid. The above-described compounds can be used singly or in combination with each other. Thus, the composition of the invention may contain potassium ions, or ammonium ions, or both the potassium and ammonium ions.

The measuring composition of the invention comprises GK and G6PDH and further contains potassium or ammonium salts, and can be used in determination of glucose, CPK, ATP or other components in a living body. Other components to be added to the composition of the invention can be chosen appropriately depending on the type of test sample to be determined.

The concentration of each component in the measuring composition of the invention is as follows:

GK:

0.1 to 20 unit/ml, preferably 0.2 to 15 unit/ml, and most preferably 0.3 to 10 unit/ml,

G6PDH:

0.1 to 20 unit/ml, preferably 0.15 to 15 unit/ml, and most preferably 0.2 to 10 unit/ml, Substrate for phosphotransferase to be measured:

0 to 100 mM, preferably 0 to 60 mM, and most preferably 0 to 40 mM,

Substrate for C-A to be measured:

0 to 100 mM, preferably 0 to 60 mM, and most preferably 0 to 40 mM,

ADP:

0 to 20 mM, preferably 0 to 15 mM, and most preferably 0 to 10 mM,

ATP:

0 to 20 mM, preferably 0 to 15 mM, and most preferably 0 to 10 mM,

Glucose:

0 to 40 mM, preferably 0 to 30 mM and most preferably 0 to 25 mM,

NAD or NADP:

0.1 to 10 mM, preferably 0.2 to 7 mM, and most preferably 0.3 to 5 mM,

Salt containing magnesium:

0.1 to 50 mM, preferably 0.5 to 20 mM, and most preferably 1 to 10 mM, and

Potassium and/or ammonium ion:

0.1 mM to 2M, preferably 0.2 to 100 mM, and most preferably 0.5 to 50 mM.

In preparing the measuring composition of the invention, the above-described components are dissolved in a 10 to 500 mM, preferably 20 to 300 mM, and most preferably 30 to 150 mM buffer (pH: 5–10), such as trishydrochloric acid and imidazole-acetic acid so that the concentration of each component is within the range as described above.

The measuring composition of the invention is applicable not only to the determination of glucose, CPK, ATP, etc., which are important measuring items for clinical analysis, but also to the determination of activity of phosphotransferase, GA, etc.

Since, in the composition of the invention, potassium or ammonium ions activate the coupling enzyme reaction, the measuring time can be shortened even if the amount of enzyme used in the reagent for measurement is decreased, and the stability at room temperature of the reagent in the state of a solution can be increased. This presents advantages in that a large amount of reagent can be prepared at one time, operation efficiency is improved, and in that the frequency of discarding surplus reagent can be decreased.

The present invention is described in greater detail with reference to the following examples and comparative examples. However, the scope of the invention is not limited to these examples.

EXAMPLE 1

A glucose-measuring composition having the formulation as described below was prepared.

| | |
|---|---|
| Heat stable GK produced by *Bacillus stearothermophilus* NCA 1503 | 2 unit/ml |
| Heat stable G6PDH produced by the same strain as above | 2 unit/ml |
| NADP.sodium salt | 2 mM |
| ATP.disodium salt | 2 mM |
| Magnesium chloride ($MgCl_2$) | 2 mM |
| Potassium chloride | 50 mM |
| Sodium azide | 10 mM |
| Tris-hydrochloric acid buffer (pH: 8.5) | 100 mM |

Using the above-prepared measuring composition, the concentration of glucose in a control serum, the glucose concentration of which had been known to be 200 mg/dl, was measured by the end point method.

That is, 0.6 ml of the measuring composition maintained at 30° C. was placed in a cell having an optical path of 1 cm, and the absorbance ($A_0$) at 340 nm was measured by the use of a spectrophotometer also maintained at 30° C.

Then, 4 µl of the specimen was added to the cell, and the enzymatic reaction was allowed to proceed. After 10 minutes, the absorbance (A) at 340 nm was measured.

The concentration of glucose in the sample was calculated from the following equation:

Concentration of Glucose (mg/dl)=437 (A-$A_0$)

The measuring composition was stored at 25° C. for one week and also for one month. At the end of each period, the concentration of glucose in the control serum was measured using the measuring composition.

The results are shown in Table 1.

COMPARATIVE EXAMPLE 1

The procedure of Example 1 was repeated wherein potassium chloride was not added.

The results are shown in Table 1.

It can be seen from Table 1 that in Example 1 all the glucose concentration values determined at the day when the measuring composition is prepared, after one-week storage at 25° C., and after one-month storage at 25° C. are nearly the same, and that the addition of potassium ions according to the present invention produces a stabilization effect.

In Comparative Example 1, since the rate of reaction was low, 10 minutes was required for the measurement. However, in Example 1, even the measurement after 3 minutes gave the same concentration value as after 10 minutes.

EXAMPLE 2

The procedure of Example 1 was repeated wherein the concentrations of GK and G6PDH were reduced to ⅓.

The results are shown in Table 1.

COMPARATIVE EXAMPLE 2

The procedure of Example 2 was repeated wherein potassium chloride was not added.

The results are shown in Table 1.

It can be seen from Table 1 that in Example 2 nearly the same concentration values as in Example 1 can be obtained, and that the concentration of enzyme can be reduced with the same results.

Also in Example 2, a reaction time of 3 minutes was sufficient.

TABLE 1

| Run No. | Glucose Concentration Values (mg/dl) | | |
| --- | --- | --- | --- |
| | Just after Preparation | After One-Week Storage | After One-Month Storage |
| Example 1 | 198 | 203 | 201 |
| Example 2 | 200 | 197 | 199 |
| Comparative Example 1 | 186 | 164 | 98 |
| Comparative Example 2 | 140 | 89 | 63 |

EXAMPLE 3

A CPK measuring composition having the formulation as described below was prepared.

| | |
| --- | --- |
| Heat stable GK (same as in Example 1) | 3 unit/ml |
| Heat stable G6PDH (same as in Example 1) | 3 unit/ml |
| ADP.disodium salt | 1 mM |
| Glucose | 12 mM |
| NADP.sodium salt | 1.6 mM |
| Magnesium acetate | 5 mM |
| AMP.disodium salt | 4 mM |
| Dithiothreitol | 10 mM |
| Sodium azide | 10 mM |
| Creatine phosphate | 20 mM |
| Ammonium sulfate | 20 mM |
| Imidazole-acetate buffer (pH: 6.7) | 100 mM |

0.6 ml of the measuring composition maintained at 30° C. was placed in a cell having an optical path of 1 cm, and then 40 µl of a commercially available control serum was added thereto. Based on changes in absorbance at 340 nm as determined using a spectrophotometer maintained at 30° C., the CPK activity of the specimen was determined.

The measuring composition was stored at 25° C. for a predetermined period of time: 6 days, 10 days, and 14 days. At the end of each period, the CPK activity was measured using the measuring composition. The CPK activity value was indicated as a relative value with that as determined using a fresh measuring composition as 100%.

The results are shown as Curve 1 in the Figure.

COMPARATIVE EXAMPLE 3

The procedure of Example 3 was repeated wherein ammonium sulfate was not added.

The results are shown as Curve 3 in the Figure.

EXAMPLE 4

The procedure of Example 3 was repeated wherein the concentrations of GK and G6PDH were reduced to ⅓.

The results are shown as Curve 2 in the Figure.

COMPARATIVE EXAMPLE 4

The procedure of Example 4 was repeated wherein ammonium sulfate was not added.

The results are shown as Curve 4 in the Figure.

It can be seen from the Figure that the measuring composition of the present invention is stable over long periods of time.

EXAMPLE 5

A glucose-measuring composition was prepared in the same manner as in Example 1 except that 2 unit/ml of G6PDH produced by *Leuconostoc mesenteroides* was used.

Using the above-prepared composition, the concentration of glucose was measured in the same manner as in Example 1 with nearly the same results as in Example 1.

While the invention has been described in detail and with reference to specific embodiments thereof, it will be apparent to one skilled in the art that various changes and modifications can be made therein without departing from the spirit and scope thereof.

What is claimed is:

1. A reagent composition for measuring glucose, which reagent composition is stable at room temperature for at least one week, said reagent composition comprising: glucokinase; glucose-6-phosphate dehydrogenase; adenosine-5'-triphosphate; β-nicotinamide-adenine dinucleotide (phosphate); and ions selected from the group consisting of potassium ions and ammonium ions, said ions being present in said composition in a concentration of 0.1 mM to 50 mM.

2. A reagent composition as claimed in claim 1, wherein the glucokinase is produced by *B. stearothermophilus*.

3. A reagent composition as claimed in claim 1, wherein the ions are present in a concentration range of 0.2 mM to 50 mM.

4. A reagent composition as claimed in claim 1, wherein the ions are produced from a salt of an acid selected from the group consisting of carbonic acid, hydrochloric acid, sulfuric acid, phosphoric acid, and acetic acid.

5. A reagent composition as claimed in claim 1, wherein said ions are potassium ions.

6. A reagent composition as claimed in claim 1, wherein said ions are ammonium ions.

7. A reagent composition as claimed in claim 6, wherein said ions are potassium ions.

8. A reagent composition for measuring creatine phosphokinase, which reagent composition is stable at room temperature for at least one week, said reagent composition comprising: glucokinase; glucose-6-phosphate dehydrogenase; glucose; adenosine-5'-diphosphate; β-nicotinamide-adenine dinucleotide (phosphate); creatine phosphate and ions selected from the group consisting of potassium ions and ammonium ions, said ions being present in said composition in a concentration of 0.1 mM to 50 mM.

9. A reagent composition as claimed in claim 8, wherein said ions are ammonium ions.

10. A method of stabilizing a reagent composition for measuring glucose, to provide a reagent composition which is stable at room temperature for at least one week, said reagent composition comprising: glucokinase; glucose-6-phosphate dehydrogenase; adenosine-5'-triphosphate; and β-nicotinamide-adenine dinucleotide (phosphate); said method comprising adding to said composition ions selected from the group consisting of potassium ions and ammonium ions, said ions being present in said composition in a concentration of 0.1 mM to 50 mM.

11. The method according to claim 10, wherein said ions are potassium ions.

12. The method according to claim 10, wherein said ions are ammonium ions.

13. A method of stabilizing a reagent composition for measuring creatine phosphokinase, which reagent is stable at room temperature for at least one week, said reagent composition comprising: glucokinase; glucose-6-phosphate dehydrogenase; glucose; adenosine-5'-diphosphate; β-nicotinamide-adenine dinucleotide (phosphate); and creatine phosphate; said method comprising adding to said composition ions selected from the group consisting of potassium ions and ammonium ions, said ions being present in said composition in a concentration of 0.1 mM to 50 mM.

14. The method according to claim 13, wherein said ions are potassium ions.

15. The method according to claim 13, wherein said ions are ammonium ions.

* * * * *